US009066996B1

(12) United States Patent
Zhou et al.

(10) Patent No.: US 9,066,996 B1

(45) Date of Patent: Jun. 30, 2015

(54) METHOD TO CONTROL THE BIODEGRADATION RATES OF POLYMER STRUCTURES

(75) Inventors: Chaoyin Zhou, Chino Hills, CA (US); Alan J. Jacobsen, Woodland Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 1143 days.

(21) Appl. No.: 12/687,875

(22) Filed: Jan. 15, 2010

Related U.S. Application Data

(63) Continuation-in-part of application No. 12/109,262, filed on Apr. 24, 2008, now Pat. No. 8,287,895.

(51) Int. Cl.

| | |
|---|---|
| ***A61F 2/00*** | (2006.01) |
| ***A61L 27/56*** | (2006.01) |
| ***C12M 1/12*** | (2006.01) |

(52) U.S. Cl.

CPC ................ *A61L 27/56* (2013.01); *C12M 25/14* (2013.01)

(58) Field of Classification Search

None

See application file for complete search history.

(56) References Cited

U.S. PATENT DOCUMENTS

| | | | | |
|---|---|---|---|---|
| 7,268,205 | B2 | 9/2007 | Williams et al. | |
| 7,382,959 | B1 | 6/2008 | Jacobsen | |
| 7,524,513 | B2 * | 4/2009 | Hai-Quan et al. | 424/443 |
| 7,906,135 | B2 * | 3/2011 | Williams et al. | 424/423 |
| 8,017,193 | B1 | 9/2011 | Zhou et al. | |
| 2007/0005140 | A1 * | 1/2007 | Kim et al. | 623/17.16 |

OTHER PUBLICATIONS

David Kisailus et al, Three-Dimensional Biological Scaffold and Method of Making the Same, Filed Apr. 24, 2008, U.S. Appl. No. 12/109,262.

Alan J. Jacobsen et al., Composite Structures With Ordered Three-Dimensional (3D) Continuous Interpenetrating Phases, Filed Jan. 11, 2008, U.S. Appl. No. 12/008,479.

Chaoyin Zhou et al., Monomer Composition for Making Polymer Waveguides, Filed Aug. 6, 2008, U.S. Appl. No. 12/187,201.

Alan J. Jacobsen, Three-Dimensional Ordered Open-Cellular Structures, Filed May 10, 2007, U.S. Appl. No. 11/801,908.

Scott J. Hollister, Porous scaffold design for tissue engineering, Nature Materials, vol. 4, Jul. 2005, pp. 518-524.

A. Khademhosseini et al., Microscale Technologies for Tissue Engineering and Biology, PNAS Feb. 21, 2006: vol. 103, No. 8, pp. 2480-2487.

* cited by examiner

*Primary Examiner* — Robert Yamasaki

(74) *Attorney, Agent, or Firm* — Christopher R. Balzao

(57) ABSTRACT

Methods to selectively control the bio-degradation rates of biologically compatible microstructures and methods to control the bio-degradation rates of three-dimensional biological scaffolds, such as ordered open-cellular polymer structures used as biological growth templates are disclosed. Medical uses and application of these materials are disclosed.

19 Claims, 4 Drawing Sheets

METHOD TO CONTROL THE BIODEGRADATION RATES OF POLYMER STRUCTURES

CROSS-REFERENCE TO RELATED APPLICATIONS

This application is a Continuation-in-part of U.S. Ser. No. 12/109,262, filed Apr. 24, 2008 now U.S. Pat. No. 8,287,895, entitled THREE-DIMENSIONAL BIOLOGICAL SCAFFOLD AND METHOD OF MAKING THE SAME; by David Kisailus, Alan Jacobsen, and Chaoyin Zhou, herein incorporated by reference in its entirety.

This application is related to the following U.S. patent applications, all hereby incorporated by reference in their entireties:

- U.S. Ser. No. 11/580,335, filed on Oct. 13, 2006 entitled OPTICALLY ORIENTED THREE-DIMENSIONAL POLYMER MICROSTRUCTURES, by Jacobsen, issued as U.S. Pat. No. 7,382,959 on Jun. 3, 2008;
- U.S. Ser. No. 12/156,380, filed on May 29, 2008 entitled OPTICALLY ORIENTED THREE-DIMENSIONAL POLYMER MICROSTRUCTURES, by Jacobsen;
- U.S. Ser. No. 11/801,908, filed on May 10, 2007 entitled THREE-DIMENSIONAL ORDERED OPEN-CELLULAR STRUCTURES, by Alan J. Jacobsen; and William B. Barvosa-Carter;
- U.S. Ser. No. 12/008,479, filed on Jan. 11, 2008, entitled: COMPOSITE STRUCTURES WITH ORDERED 3D CONTINUOUS INTERPENETRATING PHASES, by Alan J. Jacobsen, William Carter, Adam F. Gross, Robert Cumberland, Kevin W. Kirby, and David Kisailus; and
- U.S. Ser. No. 12/187,201, filed Aug. 6, 2008 entitled MONOMERIC FORMULATION FOR MAKING POLYMER WAVEGUIDES, by Chaoyin Zhou and Alan J. Jacobsen.

BACKGROUND

Control of the biodegradation rates of biologically compatible microstructures to selectively control the biodegradation rates of three-dimensional biological scaffolds, such as ordered open-cellular polymer structures, is desirable when such are used as biological growth templates.

Manufactured medical devices that are implanted in a human body have been widely used for years in medicine. The applications of implantable medical devices are numerous, including orthopedic, vascular and biomedical research.

In clinical medicine, conventional use of metals, for example, steel and titanium, are common as implantable medical devices due to their mechanical strength. Typically, in surgeries that require fixing fractures, these implantable medical devices can be used to address bone fractures by attaching a reinforcing rod or a plate to a fractured bone so that the broken ends may be stabilized to promote fusion and consequent healing. Particularly in the sports medicine area, medical devices are used to repair and augment soft tissues, such as anterior cruciate ligament (ACL) replacement. Further, implantable medical devices such as screws are used to affix bone fragments to bone structure of a patient.

A disadvantage associated with these metal implantable medical devices, however, is that they are often not biocompatible in the body, and are not biodegradable. Problems associated with these metal medical devices can include inflammation at the wound healing site, adverse affects on the surrounding tissue and, additional surgeries might be required to remove these implants from the body since they are not degradable which can be both costly and traumatic for the patient.

Recently, there has been interest in using biomaterials for the use as bioabsorbable materials in medical implants. Bioabsorbable materials can be used therapeutically, prophylactically, diagnostically and can be beneficial in the medical field.

Though metals have long been used as implantable medical devices, biodegradable materials, materials that degrade in the body, and then are absorbed into the body, have been used as an alternative to metals. Specifically designed biodegradable materials can have mechanical properties that begin to approach those of bone in some applications.

As healing progresses, the stiffness and strength of the biodegradable material implant gradually decrease, transferring loads from the implant to the healing bone tissue. Recently, synthetic polymers have been used as biodegradable materials in an implantable medical device. Such polymers include, for example, poly(glycolide), poly(lactide), I-polyactic-polyglycolic acids (PLGA) and I-polyactic acids (I-PLA). Often, however, these polymers, can be slow to degrade, often taking over one year to be absorbed by the body. Several of these polymers have been used as medical device and have controlled degradation rates. These controlled degradation rates, however, typically are based on the chemistry of their original polymer structure, often decreasing their mechanical strength in vivo and possibly altering their backbone structure. Additionally, once these polymers are implanted in the body, there is often no control on the rate of degradation.

Currently, there has been interest in scaffold-based biological tissue engineering requiring the formation of new tissues, which is strongly dependent on the three-dimensional environment provided by the scaffold. Characteristics of the scaffold that can influence the three-dimensional environment include its composition, its porous architecture, and its biological response to surrounding tissues/cellular media.

Despite the availability of these biodegradable synthetic polymers, there is a need to develop biodegradable polymers, which can further extend the range of available properties, yet perform their function in vivo while maintaining their mechanical properties while being degraded. It would be desirable to have biodegradable polymers that one skilled in the art could selectively control the rate of degradation. It would be ideal to have polymer with selective degradation rates of less than one year. In addition, it would be desirable to have a three dimensional biological polymer scaffold, with a micro-truss type cellular architecture than can be tuned to have specific mechanical properties and degradation times. Such three-dimensional biological scaffolds that can enable specific/tissue cell growth can be well suited for use as a medical implant device that could degrade over a predetermined period of time.

SUMMARY

Various embodiments provide a method for selectively controlling degradation of a three-dimensional biological scaffold. According to an embodiment, this method involves providing a three-dimensional biodegradable biological scaffold in an aqueous medium, wherein the scaffold is a polymer structure; subjecting the scaffold to a treatment capable of selectively degrading the three-dimensional biological scaffold, the treatment selected from the group consisting of base, acid, oxidation, heat and combinations thereof; and incubating the scaffold under conditions sufficient to selectively permit the degradation of the three-dimensional biological scaffold to create a partially degraded biodegradable biocompatible biological scaffold.

In one embodiment, the base treatment may include an effective amount of base which may be selected from the group consisting of sodium hydroxide, potassium hydroxide, lithium hydroxide, sodium carbonate, potassium carbonate, lithium carbonate, barium hydroxide, cesium hydroxide, strontium hydroxide, calcium hydroxide, pyridine, ammonia, and mixtures thereof. The base may be present at a concentration in aqueous solution between about a micromolar to about molar level. The base may be present between about 10 micrograms to about 10 milligrams for every milligram of polymer structure. In one embodiment during the incubating step, the biological scaffold is treated between about 10 minutes to about 1 hour with agitation.

In another embodiment, the acid treatment may include an effective amount of acid selected from a group consisting of hydrochloric acid, sulfuric acid, nitric acid, phosphoric acid, acetic acid and mixtures thereof. The acid may be present at a concentration in aqueous solution between about a micromolar to about a molar level. The acid may be present between about 1 micromole to about 1 mole for every milligram of polymer structure. In one embodiment, during the incubating step, the conditions comprise temperatures between about room temperature to about 80° C.

In yet another embodiment, the oxidation treatment may include an effective amount of oxidants selected from the group consisting of potassium permanganate, potassium dichromate, ozone, hydrogen peroxide, chorite, hypochlorite, chlorate, nitric acid, pyridinium chlorochromate, osmium tetraoxide, persulfuric acid or salts, cerium (IV) salts, and mixtures thereof. The oxidant may be present at a concentration between about a mM level to about a percentage level. The oxidant may be present between about 1 micromole and 1 mole for every milligram of polymer structure. In one embodiment, during the incubating step, the biological scaffold can be treated, between about 1 minute to about 1 hour, with agitation at room temperature.

In still yet another embodiment, the heat treatment may include an effective amount of heat at temperatures from about 80° C. to about 250° C.

In one embodiment, the three-dimensional biological scaffold may be a three-dimensional ordered open-cellular polymer structure.

In some embodiments, the three-dimensional ordered open-cellular polymer structure is a polymer biological growth template. The polymer biological growth template may be made from a monomer composition, the monomer composition includes a plurality of unsaturated molecules; a molecule having a structure of R—X1-H, wherein X1 is one of O, S, or N; and a photoinitiator; wherein each of the unsaturated molecules comprises C═X2 double bonds or C≡X2 triple bonds, wherein X2 is one of C, N, O, or S. The unsaturated groups may be selected from at least one of ethynyl, cyanide, vinyl ether, vinyl ester, vinyl amides, vinyl triazine, vinyl isocyanurate, acrylate, methacrylate, diene, or triene. The unsaturated molecules may be selected from one of pentaerythritol tetraacrylate; 2,4,6-triallyloxy-1,3,5-triazine; triallyl-1,3,5-triazine-2,4,6-trione; or tricyclohexane.

In yet another embodiment, a medical implant device made by the method for selectively controlling degradation of a three-dimensional biological scaffold, the method comprising providing a three-dimensional biodegradable biological scaffold in an aqueous medium, wherein the scaffold is a polymer structure; subjecting the scaffold to a treatment capable of selectively degrading the three-dimensional biological scaffold, the treatment selected from the group consisting of base, acid, oxidation, heat and combinations thereof; incubating the scaffold under conditions sufficient to selectively permit the degradation of the three-dimensional biological scaffold to create a partially degraded biodegradable biocompatible biological scaffold. In some embodiments, the method may further include sterilizing the partially degraded biodegradable biocompatible biological scaffold and inserting the partially degraded biodegradable biocompatible biological scaffold into living tissue.

DESCRIPTION OF THE DRAWINGS

These and other features, aspects, and advantages of various embodiments will become better understood with reference to the following description, appended claims, and accompanying drawings where:

DESCRIPTION

Figure 1:
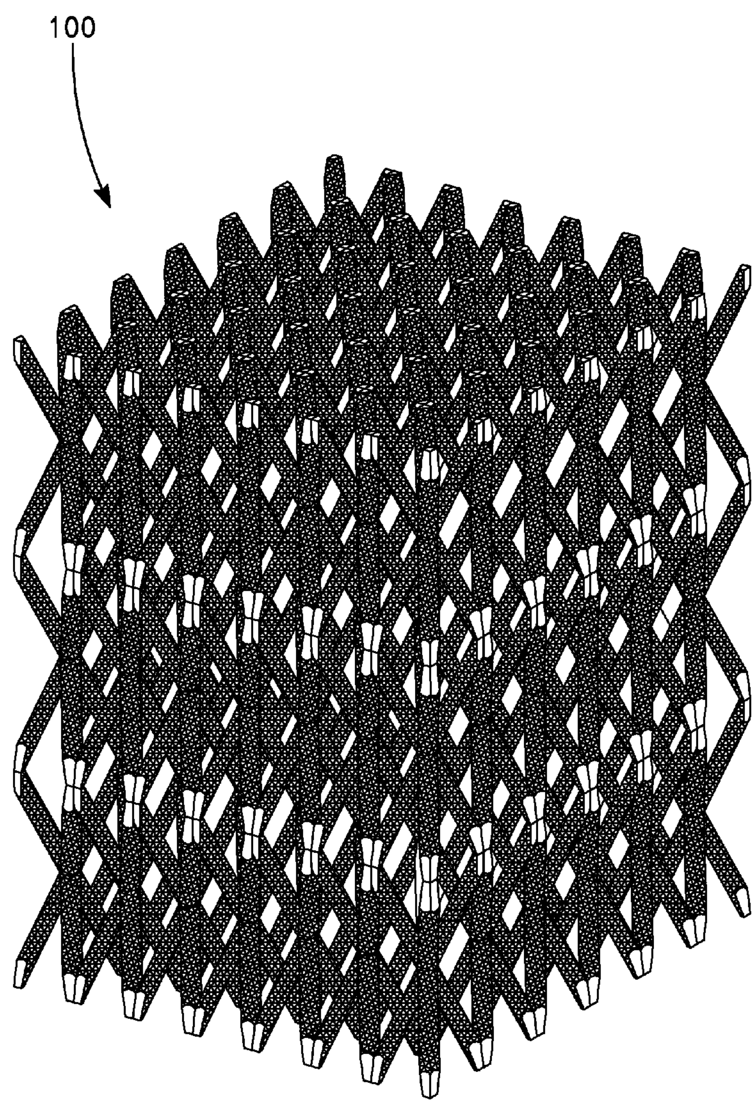
FIG. 1 illustrates an exemplary structure of a three-dimensional biological polymer scaffold.

Various embodiments provide a method for selectively controlling degradation of a three-dimensional biological scaffold. According to one embodiment, this method involves providing a three-dimensional biodegradable biological scaffold in an aqueous medium, wherein the scaffold is a polymer structure; subjecting the scaffold to a treatment capable of selectively degrading the three-dimensional biological scaffold, the treatment selected from the group consisting of base, acid, oxidation, heat and combinations thereof; and incubating the scaffold under conditions sufficient to selectively permit the degradation of the three-dimensional biological scaffold to create a partially degraded biodegradable biocompatible biological scaffold.

The controlled degradation of the three-dimensional biological scaffold can be achieved by the treatments of the structures by using the methods described herein or their combinations. In one embodiment, the three-dimensional biodegradable biological scaffold is a polymer structure. Any polymeric structure that is a biodegradable and biocompatible can participate in the controlled degradation process.

In another embodiment, the three-dimensional biological scaffold used in the present invention may be biodegradable. Without implying a limitation, as used herein, the term "biodegradable" means being capable of completely or substantially degraded or eroded when exposed to either an in vivo environment or an in vitro environment having physical, chemical, or biological characteristics substantially similar to those of the in vivo environment within a given organism, preferably a mammal. The three-dimensional biological scaffold is capable of being degraded or eroded when it can be gradually broken-down, resorbed, absorbed and/or eliminated by, for example, hydrolysis, enzymolysis, oxidation, metabolic processes, bulk or surface erosion, within the mammal.

In yet another embodiment, the partially degraded biodegradable biological scaffold is biocompatible. Without implying a limitation, as used herein, "biocompatible", means being capable of eliciting little or no immune response in a given organism, preferably a mammal, and is able to integrate with a particular cell type or tissue. In one embodiment, the partially degraded biodegradable, biocompatible biological scaffold preferably is capable of interfacing with biological systems to evaluate, treat, augment or replace any tissue, organ or function in a mammal.

In an exemplary embodiment, the three-dimensional biodegradable biological scaffold is a three-dimensional ordered open-cellular polymer structures. Preferably, the three-dimensional biological scaffold has an uniformly porous open cellular micro-truss architecture so that the degradation can be progressed uniformly. In an embodiment, the three-dimensional biodegradable biological scaffold is a three-dimensional ordered open-cellular polymer structures, which can be formed of mixtures of monomer compositions that have desirable mechanical properties, biocompatibility and degradation times within desirable time frames under physiological conditions.

Regarding the three-dimensional biodegradable biological scaffold, exemplary three-dimensional ordered open-cellular polymer structures that can be used according to an embodiment, can be made using the polymers described in U.S. patent application Ser. No. 12/187,201, entitled MONOMERIC FORMULATION FOR MAKING POLYMER WAVEGUIDES, the entire contents of which are incorporated above and herein by reference; with the process described in U.S. Pat. No. 7,382,959, entitled OPTICALLY ORIENTED THREE-DIMENSIONAL POLYMER MICROSTRUCTURES, the entire contents of which are incorporated above by reference. The structure itself is described in U.S. Ser. No. 12/156,380, filed on May 29, 2008 entitled OPTICALLY ORIENTED THREE-DIMENSIONAL POLYMER MICROSTRUCTURES, by Jacobsen, the entire contents of which are incorporated by references in its entirety as though fully set forth herein.

Figure 2:
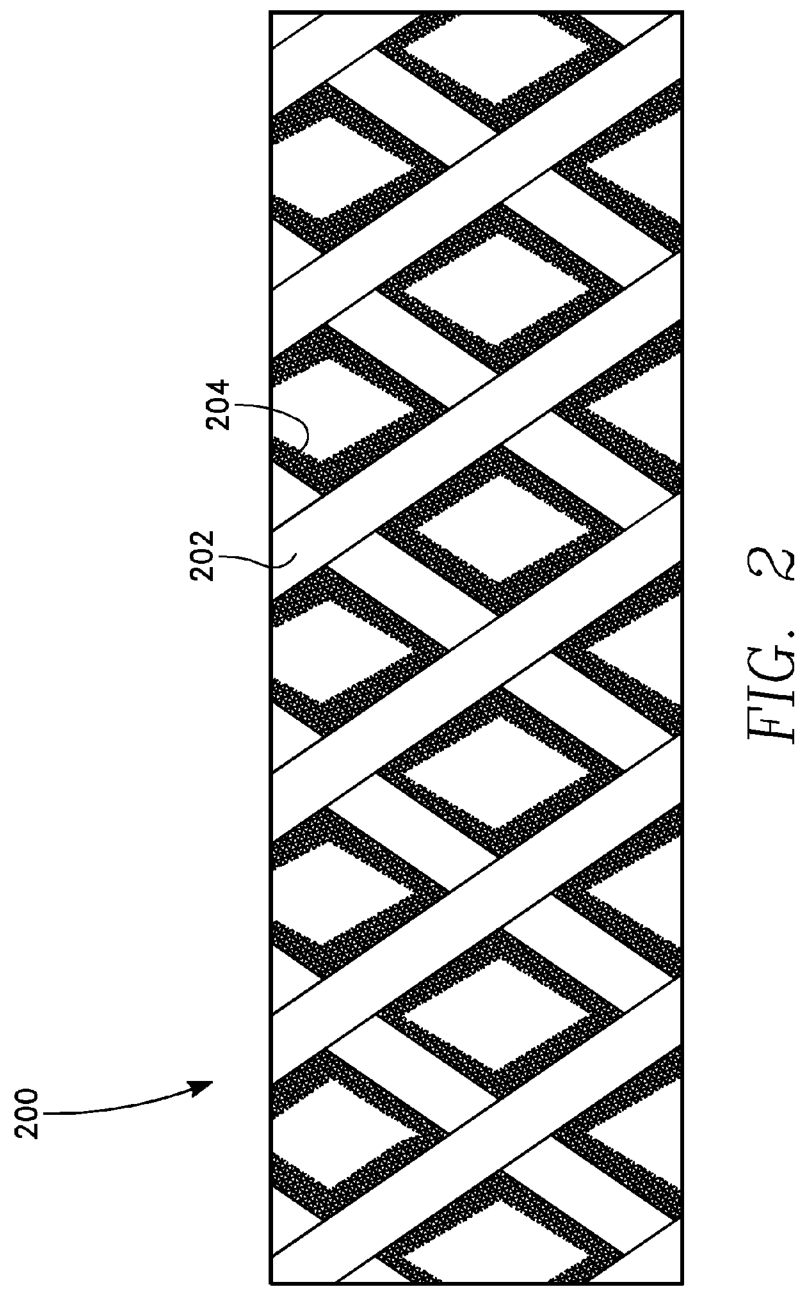
FIG. 2 illustrates a cross-sectional view of another example of a three-dimensional polymer scaffold.

FIG. 1 illustrates an exemplary structure of a three-dimensional biological polymer scaffold 100 embodiment, as disclosed in Ser. No. 12/109,262, entitled THREE-DIMENSIONAL BIOLOGICAL SCAFFOLD AND METHOD OF MAKING THE SAME FIG. 2 illustrates a partial cross-sectional exploded view of an exemplary structure of a three-dimensional biological polymer scaffold 200 pursuant to various embodiments. The three-dimensional polymer scaffold 202 can be deposited with one or more layers of material 204.

In one embodiment according to the present invention, a three-dimensional biological scaffold is provided. The three-dimensional biological scaffold preferably includes at least three sets of biodegradable self-propagating polymer waveguides extending along at least three respective directions. The at least three sets of bio-degradable polymer waveguides interpenetrate each other at a plurality of nodes to form a self-supporting structure having a plurality of ordered interconnected pores. The interpenetrations are unperturbed by changes in the index of refraction induced during fabrication. The plurality of ordered interconnected pores are sized to facilitate ingress of at least one of biological cells, vascular tissue, or nutrient media. The biodegradable polymer waveguides preferably are fabricated by photopolymerization, suitable for the construction of three dimensional open cellular polymer structures.

It is desirable to directly use a near net shaped polymer micro-truss structure formed from an interconnected pattern of self-propagating polymer waveguides as a three-dimensional biodegradable structure. Creating a micro-truss structure with the monomer formulations described in U.S. patent application Ser. No. 12/187,201, MONOMERIC FORMULATION FOR MAKING POLYMER WAVEGUIDES incorporated in its entirety, enables use of the micro-truss structure for various embodiments of this invention without the need of any additive material.

In a one embodiment, the three-dimensional ordered open-cellular polymer structure is a polymer biological growth template. Embodiments may provide the polymer biological growth template being made from a monomer composition. Preferably, the monomer composition comprises a plurality of unsaturated molecules; a molecule having a structure of R—X1-H, wherein X1 is one of O, S, or N; and a photoinitiator. Regarding the unsaturated molecules, each of the unsaturated molecules can contain multiple bonds; C═X2 double bonds or C═X2 triple bonds (e.g. X2=C, N, O, or S).

The unsaturated molecules comprise at least one of ethynyl, cyanide, vinyl ether, vinyl ester, vinyl amides, vinyl triazine, vinyl isocyanurate, acrylate, methacrylate, diene, or triene.

The unsaturated molecules are selected from one of pentaerythritol tetraacrylate; 2,4,6-triallyloxy-1,3,5-triazine; triallyl-1,3,5-triazine-2,4,6-trione; or tricyclohexane.

Advantages of using the described three-dimensional biological scaffold embodiments made from the monomer formulations, is that the molecular structure in the monomers may contain one or more different double or triple bonds, and one or more of these different structures can be used in the polymerization process. Since various combinations of double or triple bonds can be used in the polymerization process, polymer systems with very different physical properties can be created and can be chemically modified, to alter the degradation rates.

The advantages of an ordered and designed three-dimensional open-cellular (porous) structure for a biological growth template, is that the structure is ordered in a repeating pattern so that the degradation can be progressed uniformly. Typically, if the porous templates are not ordered microstructures, the degradation rate will vary between the random interconnecting struts, thereby reducing their mechanical strength asymmetrically or non homogeneously. In another embodiment, the methods provided to selectively control the degradation of three-dimensional biological scaffold, preferably the three dimensional biodegradable biological scaffold can be made from monomers and polymers that are ordered three-dimensional open-cellular polymer structures.

An advantage of some embodiments is that by selectively controlling the degradation rates of the previously disclosed biological growth template, they can now be tuned for specific tissue scaffold applications. In particular, the biological growth templates with a micro-truss-type cellular architecture can be selectively and specifically designed and tuned to have specific degradation times and a predetermined rate of degradation both in vivo and in vitro.

In a one embodiment, the biodegradable polymer can degrade under physiological conditions in less than two years, preferably less than one year both in vitro and in vivo.

According to the some embodiments, regarding the open-cellular polymer structure, by controlling the feature sizes of the ordered cellular architecture, the surface area per unit volume can be controlled. However, this can affect the degradation rate, for example when in a buffer solution at 37° C. (which simulates the physiological environment in a human body), and the degradation rates typically can be over one year.

The selectively controlled degradation of the three-dimensional biological scaffold can be achieved by the different chemical treatments of the polymeric structures by using the methods described herein or their combinations. These treatments can be performed prior to being placed in a buffer solution at 37° C. or prior to being placed in physiological environment, such as for example, the human body. By controlling and varying the parameters of these chemical treatments, (e.g. the concentrations of the bases, acids, oxidants, for example, and varying the amount of time, and temperature), the degradation of the three-dimensional biodegradable biological scaffold can be controlled and tuned to have specific degradation times. Without implying a limitation, the selectively controlled degradation times can be between weeks and months, to provide a partially degraded biocompatible scaffold that suits one skilled in the art's needs and are ideally suited for tissue scaffold applications. In addition, the different chemical treatments on the biological scaffold can significantly increase the degradation rates of these polymer scaffolds while still maintaining the micro-truss architecture.

In some embodiments, the three-dimensional biological polymer scaffold has uniform porous open cellular micro-truss architecture so that the degradation can be progressed uniformly. Typically, the porous open cellular micro-truss architecture can be lightweight and ordered.

In some embodiments, the three-dimensional biodegradable biological scaffold may be treated to enable specific functionalities, such as specific cellular recognition and proliferation needed to stimulate cell growth and achieve biocompatibility. This treated partially degraded three-dimensional biodegradable biocompatible scaffold can provide bone-implant scaffolds absorption/recognition sites for molecular/cellular species such as bone morphogenetic proteins and bi-phasic calcium phosphate that are critical for bone growth.

In one embodiment, the controlled degradation of a three-dimensional biological scaffold can be accomplished by treatments to achieve desired properties such as the controlled solubility in certain environments. During these treatments, degradation can be performed by either a chain scission, or chain weakening mechanism. Regarding the chain scission mechanism, the monomer typically is split from the main chain through depolymerization, while the chain weakening processes changes the properties of the main chain or side chain for particular applications. In one embodiment, a novel process takes advantage of both chain scission and chain weakening approaches to modify the polymer biological growth template, which ultimately controls its degradation rate in a physiological environment.

"An effective amount" as used herein is an amount that is capable of partially degrading or degrading, a compound in question.

Typically, the three-dimensional biodegradable biological scaffold just described, is provided in an aqueous medium.

In some embodiments, three-dimensional biodegradable biological scaffold can be subjected to a treatment capable of selectively degrading the three-dimensional biological scaffold. The treatment is selected from the group consisting of base, acid, oxidation, heat and combinations thereof. Next, the three-dimensional biodegradable biological scaffold can be incubated under conditions sufficient to selectively permit the degradation of the three-dimensional biological scaffold to create a partially degraded biodegradable biocompatible biological scaffold.

Figure 3:
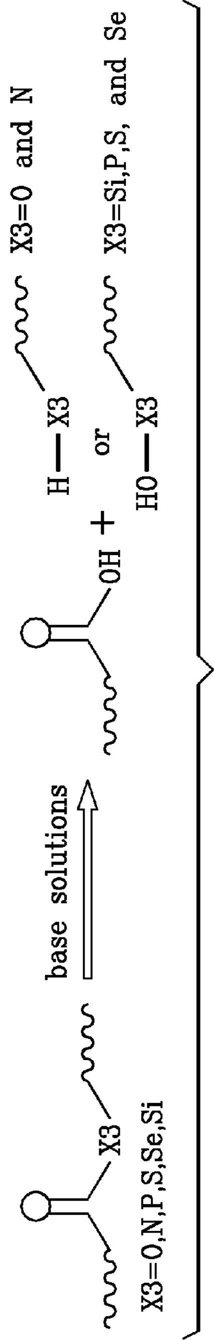
FIG. 3 illustrates an exemplary method for providing base treatment of the three-dimensional biological scaffold according to an embodiment.

FIG. 3 shows an exemplary method for providing base treatment of the three-dimensional biological scaffold according to an embodiment. The three-dimensional biodegradable biological scaffold can be treated by the basic solutions to modify the structure.

In various embodiments, the base treatment includes an effective amount of base selected from the group consisting of sodium hydroxide, potassium hydroxide, lithium hydroxide, sodium carbonate, potassium carbonate, lithium carbonate, barium hydroxide, cesium hydroxide, strontium hydroxide, calcium hydroxide, pyridine, ammonia, and mixtures thereof. In one embodiment for example, the base used is sodium hydroxide or potassium hydroxide. The aqueous solutions of the bases may be used to treat the polymeric structures.

Typically, the base is present at a concentration in aqueous solution between about micromolar to about molar level. In one embodiment, the base is between about 10 micrograms to about 10 milligrams for every milligram of polymer structure.

In one embodiment, when the three-dimensional biodegradable biological scaffold is subjected to base treatment, the biological scaffold can then be incubated under conditions sufficient to selectively permit the degradation of the three-dimensional biological scaffold to create a partially degraded biodegradable biocompatible biological scaffold. In one embodiment, the three-dimensional biological scaffold can be incubated, between about 1 minute to about 1 hour, with agitation at room temperature.

During and after the base treatment and incubation conditions, the three-dimensional ordered open-cellular polymer structures can be partially hydrolyzed and partial backbone chain scission as illustrated in FIG. 3. According to an embodiment as shown in FIG. 3, the chain scissions can occur on the surface of the polymer structures and also inside as the solution penetrates, which can be effective in degrading the polymer structure into a partially degraded biodegradable biocompatible biological scaffold.

Figure 4:
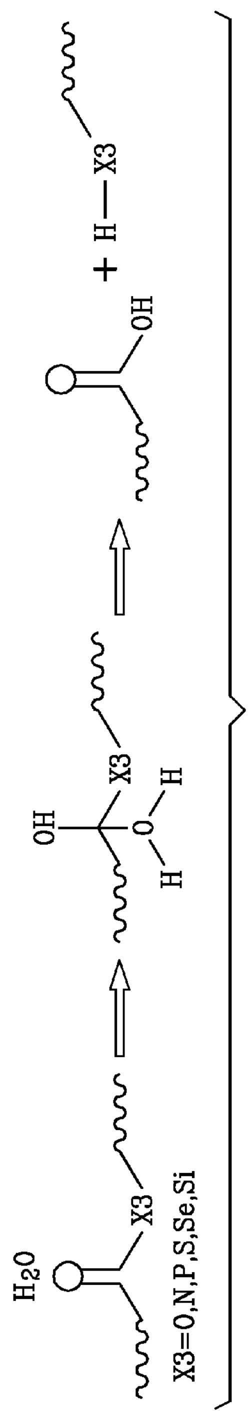
FIG. 4 illustrates an exemplary method for providing acid treatment of the three-dimensional scaffold according to an embodiment.

FIG. 4 illustrates an exemplary method for providing acid treatment of the three-dimensional scaffold according to an embodiment. The three-dimensional biodegradable biological scaffold can be treated by the acidic solutions to modify the structure.

In one embodiment, the acid treatment includes an effective amount of acid selected from the a group consisting of hydrochloric acid, sulfuric acid, nitric acid, phosphoric acid, acetic acid and mixtures thereof. The aqueous solutions of the acids may be used to treat the polymeric structures. Typically, the acid is present at a concentration in aqueous solution between about a micromolar to about a molar level.

In one embodiment, the acid is between about 1 micromole to about 1 mole for every milligram of polymer structure depending on which of the acids are used.

In an embodiment, when the three-dimensional biodegradable biological scaffold is subjected to acid treatment, the biological scaffold can then be incubated under conditions sufficient to selectively permit the degradation of the three-dimensional biological scaffold to create a partially degraded biodegradable biocompatible biological scaffold. In one embodiment, the three-dimensional biological scaffold can be incubated under conditions between about 10 minutes to about 1 hour with agitation. During the incubating step, the conditions may comprise temperatures between about room temperature to about 80° C.

During and after the acid treatment and incubation conditions, the three-dimensional ordered open-cellular polymer structures can be the hydrolyzed and breakage of C—X3 bonds can occur in the mechanism as illustrated in FIG. 4.

Typically, the acid treatment can be not as effective as the base treatment, so the treatment time typically can be longer or require higher temperatures than the base treatments. Both the base and acid treatments can degrade the polymeric structures by depolymerization through the chain scissions.

Figure 5:
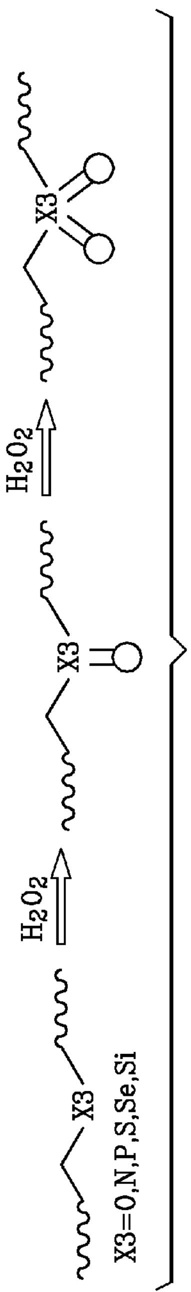
FIG. 5 illustrates an exemplary method for providing oxidation treatment of the three-dimensional biological scaffold according to an embodiment.

FIG. 5 illustrates an exemplary method for providing oxidation treatment of the three-dimensional biological scaffold according to an embodiment. The three-dimensional biodegradable biological scaffold can be treated by the oxidants to modify the structure.

In various embodiments, the oxidation treatment includes an effective amount of oxidant selected from the group consisting of potassium permanganate, potassium dichromate, ozone, hydrogen peroxide, chorite, hypochlorite, chlorate, nitric acid, pyridinium chlorochromate, osmium tetraoxide, persulfuric acid or salts, cerium (IV) salts, and mixtures thereof.

In some embodiments, the oxidation treatment can treat the three-dimensional biodegradable polymeric structures by using the oxidants in aqueous solutions.

Typically, the oxidant is present at a concentration between about a micromolar level to about a percentage level. In one embodiment, the oxidant is present between about 1 micromole and 1 mole for every milligram of polymer structure depending on the oxidants used.

In some embodiments, when the three-dimensional biodegradable biological scaffold is subjected to oxidation treatment, the biological scaffold can then be incubated under conditions sufficient to selectively permit the degradation of the three-dimensional biological scaffold to create a partially degraded biodegradable biocompatible biological scaffold. In some embodiments, the three-dimensional biological scaffold can be incubated under time conditions between about 5 minutes and 1 hour at room temperature. During the incubating step, the three-dimensional biological scaffold that is being treated can be agitated in the solution, or ultrasonically treated in the solution.

In various embodiments, the oxidation treatment of the three-dimensional ordered open-cellular polymer structures typically does not depolymerize the three-dimensional biological scaffold. In some embodiments, the oxidation process can change the functionalities on the backbone or side chain of the polymer structure, while maintaining the architecture of the main polymer structure. The properties of the polymer, however, can be significantly different.

In some embodiments, after the oxidation treatment, the partially degraded biodegradable biocompatible polymer structure typically can be softer and more malleable compared to the untreated three-dimensional biodegradable biological scaffold, although the microstructure remains intact. Typically, the oxidation treatment oxidizes the materials on preferential sites on the polymeric structure as exemplified in FIG. 5 and can change the functionalities.

According to one embodiment as illustrated in FIG. 5, when X3=S, the sulfide can be difficult to be dissolved in aqueous solutions. However, in accordance with one embodiment, treatment with an oxidant, for example, hydrogen peroxide, can convert the sulfide into sulfone, and the strong electron-withdrawing nature of the sulfonyl group can make the polymeric structure of the three-dimensional biological scaffold more susceptible to hydrolysis, which can result in a significant increase in the rate of hydrolysis and thereby the degradation rate.

In yet another embodiment, depending on the concentration and time of the oxidation treatment, for example, if hydrogen peroxide is used as the oxidant in the oxidation treatment, the sulfide can be oxidized to sulfoxide (S═O) or sulfone (—SO2-), which can exhibit a different degree of electron withdrawing capability and a different rate of hydrolysis.

In various embodiments, the control of the degradation rate of the polymeric structures can be accomplished by controlling the parameters of the oxidation treatment, such as the concentration of hydrogen peroxide solution, and the temperature and time of the treatment.

In another embodiment, an exemplary method for providing heat treatment of the three-dimensional biological scaffold is provided. The three-dimensional biodegradable biological scaffold can be treated by heat to modify the polymer structure. In one embodiment invention, the heat treatment includes an effective amount of heat at temperatures from about 80° C. to about 250° C.

In some embodiments, when the three-dimensional biodegradable biological scaffold is subjected to heat treatment, the biological scaffold can then be incubated under conditions sufficient to selectively permit the degradation of the three-dimensional biological scaffold to create a partially degraded biodegradable biocompatible biological scaffold. The amount of time the heat is applied can be varied.

During heat treatment, the three-dimensional biological scaffold that is being treated can be mechanically agitated or placed in an ultrasonic bath. The sample of three-dimensional biological scaffold can also be treated in ultrasonic without any solution.

The ability to control the degradation rate of the polymer has a distinct advantage and has applications in many areas. For example, the medical, dental, and orthopedic communities need biologically compatible structures that provide templating, porosity and interconnectivity, particularly, for example, in cell, bone, and tooth growth.

Thus, in one application, medical devices formed by the method for selectively controlling degradation of a three-dimensional biological scaffold are provided. According to one embodiment, medical devices formed from this method of selectively controlled degradation of a three-dimensional biological scaffold, involves providing a three-dimensional biodegradable biological scaffold in an aqueous medium, wherein the scaffold is a polymer structure; subjecting the scaffold to a treatment capable of selectively degrading the three-dimensional biological scaffold, the treatment selected from the group consisting of base, acid, oxidation, heat and combinations thereof; and incubating the scaffold under conditions sufficient to selectively permit the degradation of the three-dimensional biological scaffold to create a partially degraded biodegradable biocompatible biological scaffold.

It is possible in various embodiments, that the implanted medical device or partially degraded biodegradable biocompatible biological scaffold degrades after its primary function has been met. The partially degraded biological scaffolds with an ordered open-cellular polymer structure, can degrade in a predetermined period of time and can be tuned or altered and designed to have specific degradation times before they are placed, for example, in vivo. The partially degraded biodegradable biocompatible biological scaffold can degrade under physiological conditions in less than two years, preferably less than one year both in vitro and in vivo. Typically, long in vivo degradation periods of greater than one year can be undesirable since the presence of a polymer at a wound healing site can lead to inflammation. Other unforeseen problems may arise when the polymer does not decay.

Various embodiments of the implanted partially degraded biological scaffold used as a medical implant device can maintain their mechanical properties, is well tolerated by the body and will eventually degrade to non-toxic materials.

Figure 6:
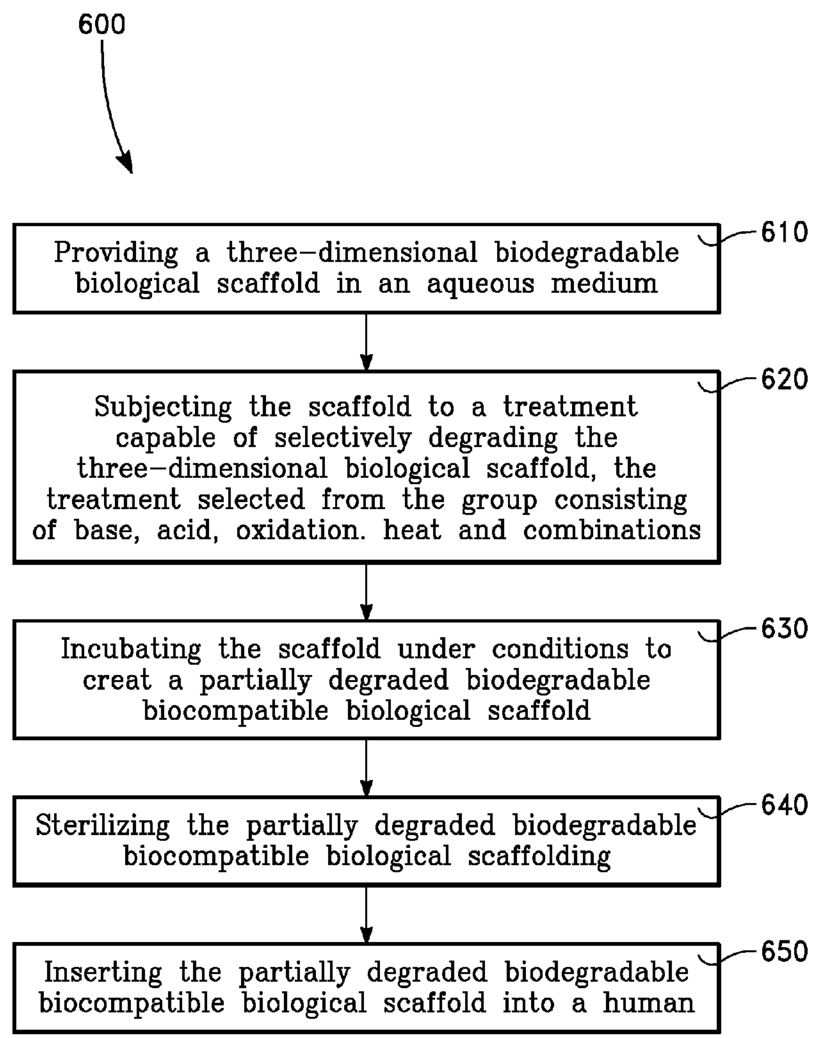
FIG. 6 is a flowchart illustrating an embodiment of a medical implant device made by the exemplary method for selectively controlling degradation of a three-dimensional biological scaffold according to an embodiment.

FIG. 6 is a flowchart illustrating an embodiment of a medical implant device made by the exemplary method 600 for selectively controlling degradation of a three-dimensional biological scaffold according to an embodiment.

In yet another embodiment, a medical implant device made by the method for selectively controlling degradation of a three-dimensional biological scaffold. The method includes providing a three-dimensional biodegradable biological scaffold having a polymer structure in an aqueous medium and subjecting the scaffold to a treatment capable of selectively degrading the three-dimensional biological scaffold, wherein the treatment is selected from the group consisting of base, acid, oxidation, heat and combinations thereof. The scaffold is incubated under conditions sufficient to selectively permit the degradation of the three-dimensional biological scaffold to create a partially degraded biodegradable biocompatible biological scaffold. The partially degraded biodegradable biocompatible biological scaffold is then sterilized, and the partially degraded biodegradable biocompatible biological scaffold may be inserted into living tissue.

The advantages of various embodiments are that by using an ordered open-cellular polymer structure that has a controlled degradation rate, as a medical device implant, the remaining scaffold structures are still well shaped after partial degradation and can be designed to be degraded in a predetermined period of time. The mechanical strength shown during degradation of these structures makes these structures desirable for biological growth template applications. In addition, the medical devices formed by various embodiments of the method to control the degradation rate of these biodegradable biocompatible polymer structures, can be tailored specifically to the type of medical device needed. One advantage of having a method to control the degradation rate of these polymer structures is that depending on what these polymers are to be used for, the medical devices can be designed to degrade in the amount of time that is needed for a particular medical device implant.

The partially degraded biodegradable biocompatible polymer structures with selectively controlled degradation in accordance with some embodiments, can be used as medical devices, and can be delivered by any means, including surgery, injection and ingestion, for example.

According to an embodiment, when these biocompatible medical devices are implanted into living tissue, there should be minimal inflammatory or adverse tissue reaction. Medical devices formed by various embodiment methods for selectively controlling degradation of a three-dimensional biological scaffold may be provided with controlled degradation rates less than one year under physiological conditions.

In some embodiments, medical devices that can be prepared using these partially degraded three-dimensional biological scaffold includes but is not limited to, tissue engineering scaffolds, medical implants, tissue regeneration devices, orthopedic devices, vascular applications, prosthetics, bone cements, orthopedic pins (including bone filling augmentation material), cartilage repair devices, nerve guides, tendon repair devices, bone marrow scaffolds, meniscus regeneration devices, ligament and tendon grafts, spinal fusion cages, skin substitutes and bone graft substitutes.

In order that the present invention may be more fully understood, the following Examples and comparative results are given by way of illustration only and not limitation.

EXAMPLES

In order to demonstrate the controlled degradation methods, the following experiments were performed:

All glassware was thoroughly cleaned in de-ionized water, rinsed in acetone, and dried in a chemical free oven at 100° C. for at least two hours, and stored in a desiccator before use.

Example 1

Three three-dimensional polymeric samples weighted approximately 70 mg, were immersed in three separate solutions of hydrogen peroxide (H2O2). The samples were contained in a glass bottle and placed in an ultrasonic bath. One was in 5% solution treated for 10 min and a second sample in a 30% solution was treated for 30 minutes while the third sample in a 30% solution was treated for 60 minutes. After the treatment in the ultrasonic bath, the samples were washed with copious amounts of distilled water and dried in air. The structure did not show any change on appearance for all three samples, but the mechanical strength became apparently different in hand tests. The sample treated in the 30% solution for 60 min was much softer than the sample treated in 30% solution for 30 min, which was also softer than the sample treated in 5% solution for 10 min. The sample in 5% solution for 10 min was not noticeably different from an untreated sample.

The samples were then put into a 0.01 M phosphate buffered saline solution (NaCl 0.138M; KCl 0.0027M) of pH 7.4 at 80° C. After 12 hrs at this temperature, all the samples from the 30%-60 min treatment were completely dissolved into the aqueous solution and the samples treated at 30%-30 min were only partially degraded. The remaining portion of the samples treated at 30%-30 min still maintained their original three-dimensional structure. For the sample with a 5%-10 min treatment, there was no apparent visual degradation.

The various previously described embodiments have many advantages. These advantages may include controlled degradation of three-dimensional biological scaffolds. The partially degraded biological scaffolds are biocompatible and biodegradable, and have high stability under physiological conditions. In particular, by controlling the degradation of these three-dimensional biological scaffolds, various embodiments offer a number of advantages in comparison to conventional polymers. These three-dimensional biological scaffolds may be ordered open-cellular biological structures that can degrade uniformly and maintain their mechanical strength. In addition, the degradation rates of the three-dimensional biodegradable biological scaffold can be controlled both in vitro and vivo. By controlling the degradation rate of these structures, these biological scaffolds can be designed to selectively degrade in a predetermined desired period of time, to suit its needs as an implant medical device. In addition, the versatility, cost effective and the applications for use as medical devices, make these methods especially valuable.

It is worthy to note that any reference to “one embodiment” or “an embodiment” means that a particular feature, structure, or characteristic described in connection with the embodiment may be included in an embodiment, if desired. The appearances of the phrase “in one embodiment” in various places in the specification are not necessarily all referring to the same embodiment.

The illustrations and examples provided herein are for explanatory purposes and are not intended to limit the scope of the appended claims. This disclosure is to be considered an exemplification of the principles of the invention and is not intended to limit the spirit and scope of the invention and/or claims of the embodiment illustrated.

Those skilled in the art will make modifications to the invention for particular applications of the invention.

The discussion included in this patent is intended to serve as a basic description. The reader should be aware that the specific discussion may not explicitly describe all embodiments possible and alternatives are implicit. Also, this discussion may not fully explain the generic nature of the invention and may not explicitly show how each feature or element can actually be representative or equivalent elements. Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation, be it a variation of any apparatus embodiment, a method embodiment, or even merely a variation of any element of these. Particularly, it should be understood that as the disclosure relates to elements of the invention, the words for each element may be expressed by equivalent apparatus terms even if only the function or result is the same. Such equivalent, broader, or even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

While the present invention has been described in connection with certain exemplary embodiments, it is to be understood that the invention is not limited to the disclosed embodiments, on the contrary, it is intended to cover various modifications and equivalent arrangements included within the spirit and scope of the appended claims, and equivalents thereof.

What is claimed is:

1. A method for selectively degrading a three-dimensional biological scaffold, comprising:

providing a three-dimensional biodegradable biological scaffold in an aqueous medium, wherein the scaffold is comprised of a polymer;

subjecting the scaffold to a treatment capable of selectively degrading the polymer, the treatment selected from the group consisting of base, acid, oxidation, heat and combinations thereof, wherein the treatment includes an effective amount of base, acid, oxidant, heat or combinations thereof that is capable of partially degrading the polymer, wherein the effective amount of heat includes temperatures between about 80° C. to about 250° C.; and incubating the scaffold under conditions which create a partially degraded three-dimensional biodegradable biocompatible biological scaffold;

wherein the three-dimensional biodegradable biocompatible biological scaffold is a three-dimensional ordered open-cellular polymer structure which (i) is formed by a plurality of polymer waveguides which interpenetrate each other at a plurality of nodes and (ii) has a micro-truss architecture comprising a repeating pattern of ordered interconnected pores;

wherein the three-dimensional ordered open-cellular polymer structure is made by photopolymerization of a monomer composition, the monomer composition comprising:

a first molecule comprising at least one C═C double bond or C≡C triple bond;

a second molecule having the structure R—$X_1$—H, wherein $X_1$ is one of O, S, or N; and a photoinitiator.

2. The method of claim 1, wherein the treatment capable of selectively degrading the polymer includes an effective amount of base selected from the group consisting of sodium hydroxide, potassium hydroxide, lithium hydroxide, sodium carbonate, potassium carbonate, lithium carbonate, barium hydroxide, cesium hydroxide, strontium hydroxide, calcium hydroxide, pyridine, ammonia, and mixtures thereof.

3. The method of claim 2, wherein the base is present at a concentration in aqueous solution between about micromolar to about molar level.

4. The method of claim 3, wherein the base is present between about 10 micrograms to about 10 milligrams for every milligram of polymer structure.

5. The method of claim 2, wherein during the incubating step, the conditions under which the biological scaffold is incubated are between about 1 minute to about 1 hour with agitation at room temperature.

6. The method of claim 1, wherein the treatment capable of selectively degrading the polymer includes an effective amount of acid selected from the group consisting of hydrochloric acid, sulfuric acid, nitric acid, phosphoric acid, acetic acid and mixtures thereof.

7. The method of claim 6, wherein the acid is present at a concentration in aqueous solution between about a micromolar to about a molar level.

8. The method of claim 7, wherein the acid is present between about 1 micromole to about 1 mole for every milligram of polymer structure.

9. The method of claim 6, wherein during the incubating step, the conditions under which the biological scaffold is incubated are between about 1 minute to about 1 hour with agitation.

10. The method of claim 6, wherein during the incubating step, the conditions comprise temperatures between about room temperature to about 80° C.

11. The method of claim 1, wherein the treatment capable of selectively degrading the polymer includes an effective amount of oxidant selected from the group consisting of potassium permanganate, potassium dichromate, ozone, hydrogen peroxide, chlorite, hypochlorite, chlorate, nitric acid, pyridinium chlorochromate, osmium tetraoxide, persulfuric acid or salts, cerium (IV) salts, and mixtures thereof.

12. The method of claim 11, wherein the oxidant is present between about 1 micromole an 1 mole for every milligram of polymer structure.

13. The method of claim 11, wherein during the incubating step, the conditions under which the biological scaffold is incubated are between about 1 minute to about 1 hour with agitation at room temperature.

14. The method of claim 1, wherein the treatment capable of selectively degrading the polymer includes an effective amount of heat.

15. The method as claimed in claim 1, wherein the first molecule comprises at least one functional group selected from the group consisting of ethynyl, vinyl ether, vinyl ester, vinyl amide, vinyl triazine, vinyl isocyanurate, acrylate, methacrylate, diene and triene.

16. The method as claimed in claim 1, wherein the first molecule is selected from the group consisting of pentaerythritol tetraacrylate; 2,4,6-triallyloxy-1,3,5-triazine; and triallyl-1,3,5-triazine-2,4,6-trione.

17. The method of claim 1, the method further comprising:

sterilizing the partially degraded biodegradable biocompatible biological scaffold; and inserting the partially degraded biodegradable biocompatible biological scaffold into living tissue.

18. A method for selectively degrading a three-dimensional biodegradable biological scaffold having an ordered open-cellular polymer structure, comprising:

providing a three-dimensional biodegradable biological scaffold having an ordered open-cellular polymer structure made by photopolymerization of monomer composition, the monomer composition comprising a first molecule comprising at least one C═C double bond or C≡C triple bond, a second molecule having a structure of R—$X_1$—H, wherein $X_1$ is one of O, S, or N, and a photoinitiator, wherein the three-dimensional ordered open-cellular polymer structure: (i) is in an aqueous medium, (ii) is formed by a plurality of self-propagating polymer waveguides which interpenetrate each other at a plurality of nodes, and (iii) has a micro-truss architecture comprising a repeating pattern of ordered interconnected pores;

subjecting the scaffold to a treatment capable of selectively degrading the three-dimensional biological scaffold, the treatment selected from the group consisting of base, acid, oxidation, heat and combinations thereof wherein the treatment includes an effective amount of base, acid, oxidant, heat or combinations thereof being capable of partially degrading the polymer, wherein the effective amount of base is selected from the group consisting of sodium hydroxide, potassium hydroxide, lithium hydroxide, sodium carbonate, potassium carbonate, lithium carbonate, barium hydroxide, cesium hydroxide, strontium hydroxide, calcium hydroxide, pyridine, ammonia, and mixtures thereof, wherein the effective amount of acid is selected from the a group consisting of hydrochloric acid, sulfuric acid, nitric acid, phosphoric acid, acetic acid and mixtures thereof, and wherein the effective amount of oxidant is selected from the group consisting of potassium permanganate, potassium dichromate, ozone, hydrogen peroxide, chlorite, hypochlorite, chlorate, nitric acid, pyridinium chlorochromate, osmium tetraoxide, persulfuric acid or salts, cerium (IV) salts, and mixtures thereof, and wherein the effective amount of heat includes temperatures from about 80° C. to about 250° C.; and incubating the scaffold under conditions sufficient to selectively degrade the polymer to create a partially degraded three-dimensional biodegradable biocompatible biological scaffold.

19. A medical implant device made by a method of selectively degrading a three-dimensional biological scaffold, the method comprising the steps of:

providing a three-dimensional biodegradable biological scaffold in an aqueous medium, wherein the scaffold is a polymer structure;

subjecting the three-dimensional biological polymer scaffold to a treatment capable of selectively degrading the polymer, the treatment selected from the group consisting of base, acid, oxidation, heat and combinations thereof, wherein the treatment includes an effective amount of base, acid, oxidant, heat or combinations thereof that is capable of partially degrading the polymer, wherein the effective amount of heat includes temperatures between about 80° C. to about 250° C.; and incubating the scaffold under conditions which create a partially degraded biodegradable biocompatible biological scaffold, wherein the three-dimensional biodegradable biocompatible biological scaffold has a three-dimensional ordered open-cellular polymer structure which (i) is formed by a plurality of self-propagating polymer waveguides which interpenetrate each other at a plurality of nodes and (ii) has a micro-truss architecture comprising a repeating pattern of ordered interconnected pores, wherein the three-dimensional ordered open-cellular polymer structure is made by photopolymerization of a monomer composition, the monomer composition comprising:

a first molecule comprising at least one C═C double bond or C≡C triple bond;

a second molecule having a structure of R—$X_1$—H, wherein $X_1$ is one of O, S, or N; and a photoinitiator.

* * * * *